United States Patent [19]

Friedman

[11] Patent Number: 6,055,494
[45] Date of Patent: Apr. 25, 2000

[54] SYSTEM AND METHOD FOR MEDICAL LANGUAGE EXTRACTION AND ENCODING

[75] Inventor: Carol Friedman, Larchmont, N.Y.

[73] Assignee: The Trustees of Columbia University in the City of New York, New York, N.Y.

[21] Appl. No.: 08/738,889

[22] Filed: Oct. 28, 1996

[51] Int. Cl.[7] .......................... G06F 17/27; G06F 159/00
[52] U.S. Cl. .................... 704/9; 705/2; 707/531
[58] Field of Search .......................... 704/1, 9, 10; 705/2, 705/3; 707/104, 531, 532, 533, 534

[56] References Cited

U.S. PATENT DOCUMENTS

| | | | |
|---|---|---|---|
| 4,965,763 | 10/1990 | Zamora | 704/1 |
| 5,251,131 | 10/1993 | Masand et al. | 704/9 |
| 5,265,065 | 11/1993 | Turtle | 707/4 |
| 5,327,341 | 7/1994 | Whalen et al. | 705/3 |
| 5,377,103 | 12/1994 | Lamberti et al. | 704/9 |
| 5,551,022 | 8/1996 | Tariq et al. | 707/104 |
| 5,809,476 | 9/1998 | Ryan | 705/2 |

OTHER PUBLICATIONS

Rita Rubin: "Can't Reach Your Doctor? Try E–mail."*U.S. News & World Report*, pp. 82–83, Feb. 13 1995.

David Bennahum: "Docs for Docs", *Wired*, pp. 100, 102 & 104, Mar. 1995.

C. Friedman et al., "A Conceptual Model for Clinical Radiology Reports". In: C. Safran, ed., *Seventeenth Symposium for Computer Applications in Medical Care*, New York, McGraw–Hill, Mar. 1994, pp. 829–833.

C. Friedman ete al., "A General Natural—Language Text Processor for Clinical Radiology", Journal of the American Medical Informatics Association, vol. 1 (Apr. 1994), pp. 161–174.

C. Friedman et al., "A Schema for Representing Medical Language Applied to Clinical Radiology", Journal of the American Medical Informatics Association, vol. 1 (Jun. 1994), pp. 233–248.

C. Freidman et al., "Natural Language Processing in an Operational Clinical Information System", Natural Language Engineering, vol. 1 (May 1995), pp. 83–108.

C. Friedman et al., "Architectural Requirements for a Multipurpose Natural Language Processor in the Clinical Enviroment". In: R.M. Gardner, ed., *Proceedings, Nineteenth Annual Symposium on Computer Applications in Medical Care*, Hanley & Belfus, Nov. 1995, pp. 347–351.

P.O. El Guedji et al., "A Chart Parser to Analyze Large Medical Corpora". In: N.F. Sheppard, Jr., et al., Proceedings of the 16th Annual International Conference of the IEEE Engineering in Medicine and Biology Society, IEEE, Nov. 1994, pp. 1404–1405.

K.P. Jones, "Artificial Intelligence Program for Indexing Automatically (AIPIA)". In: D.I. Raitt, ed., Online Information 92. 16th International Online Information Meeting Proceedings, Learned Inf Oxford, Dec. 1992, pp. 187–196.

*Primary Examiner*—Joseph Thomas
*Attorney, Agent, or Firm*—Baker & Botts L.L.P.

[57] ABSTRACT

In computerized processing of natural-language medical/clinical data including phrase parsing and regularizing, parameters are referred to whose value can be specified by the user. Thus, a computerized system can be provided with versatility, for the processing of data originating in diverse domains, for example. Further to a parser and a regularizer, the system includes a preprocessor, output filters, and an encoding mechanism.

19 Claims, 1 Drawing Sheet

SYSTEM AND METHOD FOR MEDICAL LANGUAGE EXTRACTION AND ENCODING

BACKGROUND OF THE INVENTION

This invention relates to natural language processing and, more specifically, to computerized processing of natural-language phrases found in medical/clinical data.

Clinical information as expressed by health care personnel is typically provided in natural language, e.g., in English. But, while phrases in natural language are convenient in interpersonal communication, the same typically does not apply to computerized applications such as automated quality assurance, clinical decision support, patient management, outcome studies, administration, research and literature searching. Even where clinical data is available in electronic or computer-readable form, the data may remain inaccessible to computerized systems because of its form as narrative text.

For computerized applications, methods and systems have been developed for producing standardized, encoded representations of clinical information from natural-language sources such as findings from examinations, medical history, progress notes, and discharge summaries. Special-purpose techniques have been used in different domains, e.g., general and specialized pathology, radiology, and surgery discharge reports.

Of particular further interest is a general approach which is based on concepts and techniques described in the following papers:

C. Friedman et al., "A Conceptual Model for Clinical Radiology Reports". In: C. Safran, ed., *Seventeenth Symposium for Computer Applications in Medical Care*, New York, McGraw-Hill, March 1994, pp. 829–833;

C. Friedman et al., "A General Natural-Language Text Processor for Clinical Radiology", *Journal of the American Medical Informatics Association*, Vol. 1 (April 1994), pp. 161–174;

C. Friedman et al., "A Schema for Representing Medical Language Applied to Clinical Radiology", *Journal of the American Medical Informatics Association*, Vol. 1 (June 1994), pp. 233–248;

C. Friedman et al., "Natural Language Processing in an Operational Clinical Information System", *Natural Language Engineering*, Vol. 1 (March 1995), pp. 83–106.

SUMMARY OF THE INVENTION

A preferred method for computerized processing of natural-language medical/clinical data includes basic steps here designated as phrase parsing and regularizing and, optionally, code selection. Further included, preferably, is a step of pre-processing prior to phrase parsing, and a step of output filtering. Output can be generated in the form of a printout, as a monitor display, as a database entry, or via the "information highway", for example.

In processing, one or several parameters are referred to. The parameters are associated with options. To choose an option, the appropriate value is assigned to the parameter. A parameter can have a value by default. Of particular importance is the inclusion of a parameter which is associated with the medical/clinical domain or subfield of the input data. Other parameters may be associated with the level of parsing accuracy desired, whether code selection is desired, the type of filtering, or the format of the output.

The method can be expressed in a high-level computer language such as Prolog, for example, for execution as a system on a suitable general-purpose computer. In the following, the method and the system will be referred to by the acronym MedLEE, short for Medical Language Extraction and Encoding.

An Appendix hereto includes a printout of computer source code for a portion of MedLEE.

DETAILED DESCRIPTION OF PREFERRED EMBODIMENTS

A natural-language phrase included in medical/clinical data is understood as a delimited string comprising natural-language terms or words. The string is computer-readable as obtained, e.g., from a pre-existing database, or from keyboard input, optical scanning of typed or handwritten text, or processed voice input. The delimiter may be a period, a semicolon, an end-of-message signal, a new-paragraph signal, or any other suitable symbol recognizable for this purpose. Within the phrase, the terms are separated by another delimiter, e.g., a blank or another suitable symbol.

As a result of phrase parsing, terms in a natural-language phrase are classified, e.g., as referring to a body part, a body location, a clinical condition or a degree of certainty of a clinical condition, and the relationships between the terms are established and represented in a standard form. For example, in the phrase "moderate cardiac enlargement", "moderate" is related to "enlargement" and cardiac is also related to "enlargement".

In the interest of versatility and applicability of the system to different domains, parsing is domain specific as a function of the value assigned to a parameter which the system refers to in parsing. Depending on the value of the domain parameter, the appropriate rules can be referred to in parsing by the system.

While parsing may be based primarily on semantics or meaning, use of syntactic or grammatical information is not precluded.

Regularizing involves bringing together terms which may be discontiguous in a natural-language phrase but which belong together conceptually. Regular forms or composites are obtained. Regularizing may involve reference to a separate knowledge base. For example, from each of the phrases "heart is enlarged", "enlarged heart", "heart shows enlargement" and "cardiac enlargement", a regularizer can generate "enlarged heart".

In code selection, which is optional, a common, unique vocabulary term or code is assigned to each regular term by reference to yet another knowledge base which may also be chosen domain specific. For example, in the domain of X-ray diagnostics, the term "cystic disease" has a different meaning as compared with the domain of mammography.

Figure 1:
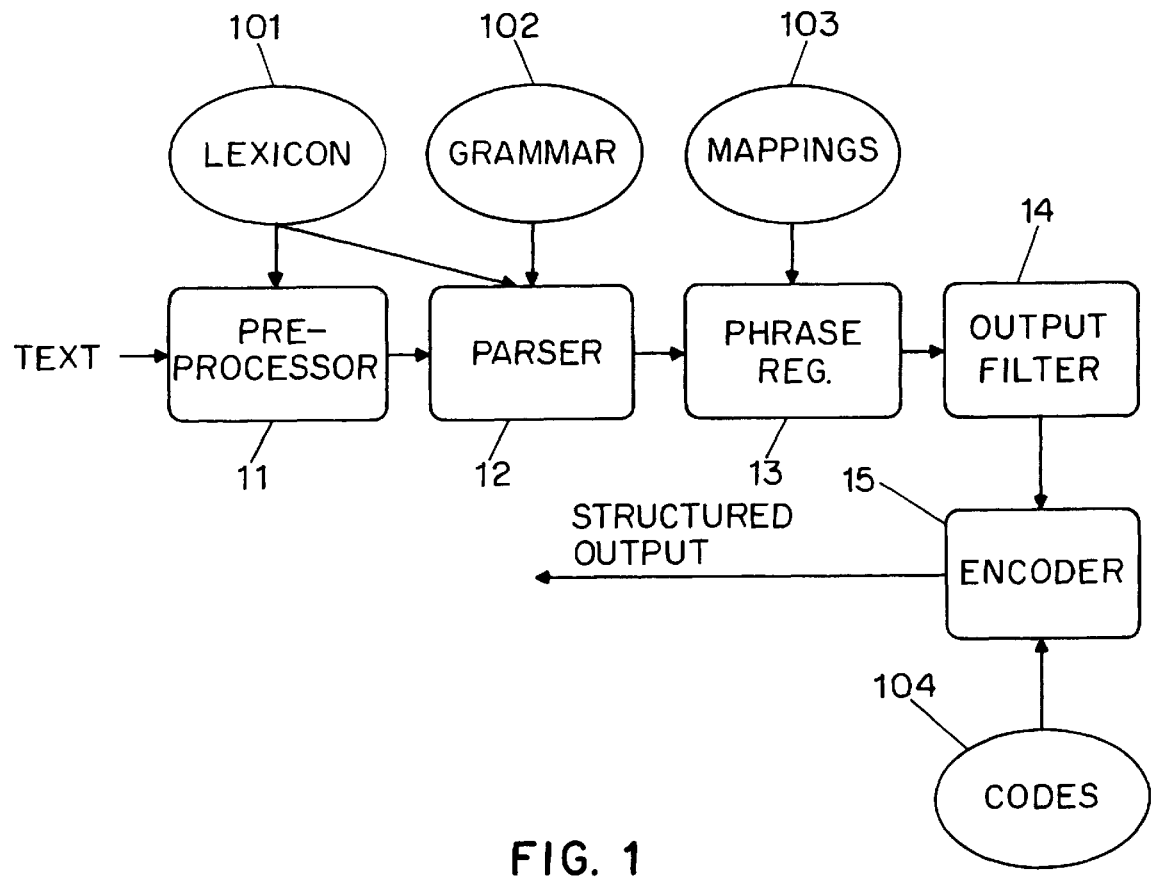
FIG. 1 is a diagram of the MedLEE system or "server".

FIG. 1 shows a preprocessor module 11 by which natural-language input text is received. The preprocessor uses the lexicon knowledge base 101 and handles abbreviations, which may be domain dependent. With the domain parameter properly set, the preprocessor refers to the proper knowledge base. For example, depending on the domain, the abbreviation "P.E." can be understood as physical examination or as pleural effusion. Also, the preprocessor determines phrase or sentence boundaries, and generates a list form for each phrase for further processing by the parser module 12.

The parser module 12 also uses the lexicon 101, and a grammar module 102 to generate intermediate target forms. Thus, in addition to parsing of complete phrases, subphrase parsing can be used to advantage where highest accuracy is not required. In case a phrase cannot be parsed in its entirety, one or several attempts can be made to parse a portion of the phrase for obtaining useful information in spite of some uncertainty. For example, subphrase parsing can be used in surveying discharge summaries.

With the parsed forms as input, and using mapping information 103, the phrase regularizer 13 composes regular terms as described above.

From the regularized phrases, the filter module 14 deletes information on the basis of parameter settings. For example, a parameter can be set to call for removal of negative findings.

The encoder module 15 uses a table of codes 104 to translate the regularized forms into unique concepts which are compatible with a clinical controlled vocabulary.

Figure 2:
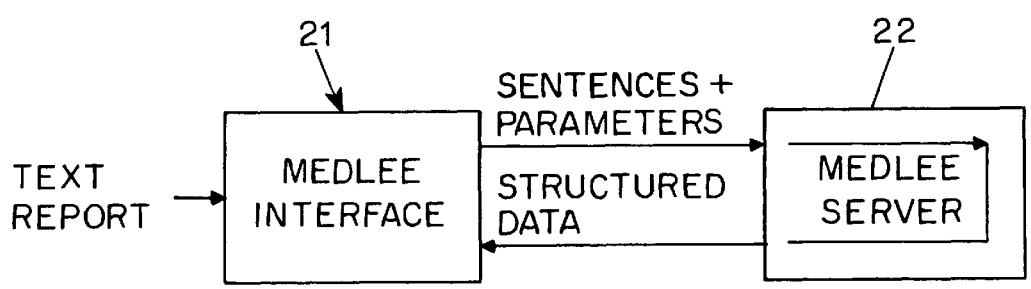
FIG. 2 is a diagram of a system or application which has an interface for MedLee.

FIG. 2 shows an interface module 21, and the MedLee system 22 of FIG. 1. The interface module 21 may be domain-specific, and it may serve, e.g., to separate formatted sections from non-formatted sections in a report. Also, the interface 22 may serve to pass chosen parameter values to the MedLEE system 22 and to pass output from the MedLEE system. For example, such an interface can be designed for communication over the World-Wide Web or a local network, for input to or output from MedLEE.

Conveniently, each module is software-implemented and stored in random-access memory of a suitable computer, e.g., a work-station computer. The software can be in the form of executable object code, obtained, e.g., by compiling from source code. Source code interpretation is not precluded. Source code can be in the form of sequence-controlled instructions as in Fortran, Pascal or "C", for example. Alternatively, a rule-based system can be used such a Prolog, where suitable sequencing is chosen by the system at run-time.

An illustrative portion of the MedLEE system is shown in the Appendix in the form of a Prolog source listing with comments. The following is further to the comments.

Process_sents with get_inputsents, process_sects and outputresults reads in an input stream, processes sections of the input stream according to parameter settings, and produces output according to the settings. Among parameters supplied to Process_sents are the following: Exam (specifying the domain), Mode (specifying the parsing mode), Amount (specifying the type of filtering), Type (specifying the output format) and Protocol (html or plain). Process_sents is called by another predicate, after user-specified parameters have been processed.

Process_sects with get_section and parse_sentences gets each section and generates intermediate output for the sentences in each section.

Outputresults with removefromtarg, write, writelines, markupsents and outputhl7 filters output if appropriate, produces output in the appropriate format and optionally including formats tags for selected words of the original sentence, and produces error messages and an end-of-output message.

Setargs sets arguments or parameter values based on user input or by default.

Removefromtarg filters formatted output by leaving only positive clinical information and by removing negative findings from the formatted output. Another parameter, parc, removes findings associated with past information from the formatted output. Any number of different filters can be included as suitable.

Writelines produces one line per finding, in list format. Writeindentform and writeindentform2 produce output in indented form.

Markupsents envelopes the original sentence with tags so that the clinical information is highlighted. Different types of information can be highlighted in different colors by use of an appropriate browser program such as Netscape, for example.

Outputhl7 converts output to appropriate form for database (xformtodb) and writes out the form in hl7 in coded format. This process uses synonym knowledge and an encoding knowledge base.

I claim:

1. A computer method for processing medical/clinical data comprising a natural-language phrase,
    the method comprising parsing the natural-language phrase and regularizing the parsed phrase,
    wherein said parsing step comprises referring to a domain parameter whose value is indicative of a medical/clinical domain from which the data originated, and wherein said domain parameter corresponds to one or more rules of grammar within a knowledge base related to said medical/clinical domain to be applied for parsing said natural language phrase.

2. The method according to claim 1, further comprising preprocessing the data prior to parsing, with preprocessing comprising referring to the domain parameter.

3. The method according to claim 1, further comprising encoding at least one term of the regularized phrase, with encoding comprising referring to the domain parameter.

4. The method according to claim 1, further comprising filtering the regularized phrase.

5. The method according to claim 1, further comprising referring to an additional parameter which is indicative of the degree to which subphrase parsing is to be carried out.

6. The method according to claim 1, further comprising referring to an additional parameter which is indicative of desired filtering.

7. The method according to claim 1, further comprising referring to an additional parameter which is indicative of a desired type of output.

8. The method according to claim 1, further comprising referring to an additional parameter which is indicative of a desired output format.

9. A computer system for processing medical/clinical data comprising a natural-language phrase,
    the system comprising means for parsing the natural-language phrase and means for regularizing the parsed phrase,
    wherein the said parsing step means comprises means for referring to a domain parameter whose value is indicative of a medical/clinical domain from which the data originated, and wherein said domain parameter corresponds to one or more rules of grammar within knowledge base related to said medical/clinical domain to be applied for parsing said natural language phase.

10. The system according to claim 9, further comprising means for preprocessing the data prior to parsing, with the preprocessing means comprising means for referring to the domain parameter.

11. The system according to claim 9, further comprising means for encoding at least one term of the regularized phrase, with the encoding means comprising means for referring to the domain parameter.

12. The system according to claim 9, further comprising means for filtering the regularized phrase.

13. The system according to claim 9, further comprising means for referring to an additional parameter which is indicative of the degree to which subphrase parsing is to be carried out.

14. The system according to claim 9, further comprising means for referring to an additional parameter which is indicative of desired filtering.

15. The system according to claim 9, further comprising means for referring to an additional parameter which is indicative of a desired type of output.

16. The system according to claim 9, further comprising means for referring to an additional parameter which is indicative of a desired output format.

17. A combination of the system according to claim 9 with an interface module for enabling the system to receive input from and/or to produce standardized output for the World-Wide Web and/or a local network.

18. The combination according to claim 17, further comprising means for viewing the output using a standardized browser.

19. The combination according to claim 18, wherein the browser is a Web-browser.

* * * * *

UNITED STATES PATENT AND TRADEMARK OFFICE
CERTIFICATE OF CORRECTION

PATENT NO.        : 6,055,494                                         Page 1 of 1
APPLICATION NO. : 08/738889
DATED             : April 25, 2000
INVENTOR(S)       : Friedman It is certified that error appears in the above-identified patent and that said Letters Patent is hereby corrected as shown below:

Column 1, line 3, please insert the following header and paragraph:

-- Statement Regarding Federally Sponsored Research or Development
This invention was made with government support under grant numbers LM006274 and LM005627 awarded by the National Institutes of Health. The government has certain rights in the invention. --

Signed and Sealed this

First Day of July, 2008

JON W. DUDAS
*Director of the United States Patent and Trademark Office*